United States Patent [19]

Janitschke et al.

[11] Patent Number: 5,523,485
[45] Date of Patent: Jun. 4, 1996

[54] PREPARATION OF HIGH-PURITY ISOBUTYRAMIDE

[75] Inventors: Lothar Janitschke, Kleinniedesheim; Ernst Buschmann, Ludwigshafen, both of Germany

[73] Assignee: BASF Aktiengesellschaft, Ludwigshafen, Germany

[21] Appl. No.: 355,288

[22] Filed: Dec. 12, 1994

[30] Foreign Application Priority Data

Dec. 17, 1993 [DE] Germany .................. 43 43 175.5

[51] Int. Cl.$^6$ ............................................. C07C 231/02
[52] U.S. Cl. .................. 564/143; 564/133; 564/134; 564/142; 564/215
[58] Field of Search ................... 564/215, 133, 564/134, 142, 143

[56] References Cited

U.S. PATENT DOCUMENTS 3,901,908  8/1975  Fitzi et al. ........................ 260/309

OTHER PUBLICATIONS

S. P. Perrine, D. V. Faller, Experientia 49 (1993) 133.
N. O. V. Sonntag, Chem. Revs. 52 (1953) 237.
O. Aschan, Chem. Ber. 31 (1898) 2348.
Organic Synthesis, Coll. vol. III, 490–492, 1955.
G. E. Philbrook (J. Org. Chem. 19 (1954) (623).

*Primary Examiner*—Shailendra Kumar
*Attorney, Agent, or Firm*—Keil & Weinkauf

[57] ABSTRACT

A process for preparing high-purity isobutyramide which comprises reacting isobutyryl chloride in toluene or xylene at −15° to 30° C. with ammonia is described.

2 Claims, No Drawings

PREPARATION OF HIGH-PURITY ISOBUTYRAMIDE

BACKGROUND OF THE INVENTION

1. Field of the Invention

Isobutyramide is of interest as a therapeutic agent for sickle cell anemia (S. P. Perrine, D. V. Faller, Experientia 49 (1993) 133). The dose of the active substance required for therapy is extremely high. This is why the purity of this substance is required to be particularly high.

The preparation of isobutyramide and related amides has been described many times in the literature: Houben-Weyl, Methoden der Organischen Chemie. Volume VIII, pages 655 et seq., N.O.V. Sonntag, Chem. Revs. 52 (1953) 237.

2. Description of Related Art

The simplest method for preparing these amides is to react acid chlorides with aqueous ammonia: O. Aschan, Chem. Ber. 31 (1898) 2348, R. E. Kent, S. M. McElvain, Organic Synthesis, Coll. Vol. III, 490–492). However, the Aschan method provides low yields. Better yields are obtained by the Kent-McElvain process.

However, this process requires multistage isolation of the product. The purity achieved thereby does not meet clinical requirements.

Good yields are obtained in a non-aqueous process described by G. E. Philbrook (J. Org. Chem. 19 (1954) 623).

This entails dropwise addition of isobutyryl chloride to a solution of ammonia in benzene. Since the solubility of ammonia in benzene is only low, a stream of gaseous ammonia is passed through the solution throughout the addition time.

Attempts to simplify the process by introducing ammonia as gas or in liquid form into the acid chloride lead, according to G. E. Philbrook, to formation of large amounts of the diamide I.

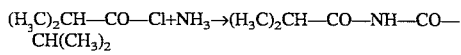

$(H_3C)_2CH-CO-Cl+NH_3 \rightarrow (H_3C)_2CH-CO-NH-CO-CH(CH_3)_2$

Traces of isobutyronitrile are formed in the preparation of isobutyramide. Removal of isobutyronitrile by distillation is difficult when the benzene is reused as solvent, so that this byproduct accumulates on repeated use of the benzene. However, the highly toxic nitrile must not be present even in the smallest traces in isobutyramide used for medicinal purposes.

SUMMARY OF THE INVENTION

We have now found a simple process for preparing isobutyramide.

The invention relates to a process for preparing high-purity isobutyramide from isobutyryl chloride and ammonia, which comprises adding ammonia to a solution of isobutyryl chloride in toluene or xylene at −15° to 30° C., subsequently heating the mixture, removing the ammonium chloride which is formed by hot filtration, and allowing isobutyramide to crystallize out of the organic solution.

DESCRIPTION OF THE PREFERRED EMBODIMENTS

The ammonia is added at from about −10° to +30° C. Addition expediently starts at about −10° C. The temperature rises during the addition of the ammonia. The addition rate and cooling are adjusted so that the reaction temperature does not exceed 30° C. Ammonia can be introduced as gas into the solution of isobutyryl chloride or be added dropwise in liquid form. After the addition of ammonia, the reaction mixture is heated in order to keep all the isobutyramide in solution.

An expedient temperature is from 80° C. to the temperature at which the solvent refluxes, preferably from 100° C. to the reflux temperature.

The molar ratio of the amounts of ammonia to isobutyryl chloride used in the reaction is about 2:1 to 4:1.

The resulting ammonium chloride is expediently removed by filtration. The solution is subsequently concentrated to about 30–70% of its volume and cooled to about room temperature or below. The isobutyramide then separates out.

The use of toluene or xylene makes it possible to introduce ammonia into the solution of isobutyryl chloride without producing interfering amounts of diamide.

In contrast to the process disclosed by Philbrook, when xylene and toluene are used it is possible much more straightforwardly to remove traces of isobutyronitrile by distillation.

The novel process has the further advantage that the resulting ammonium chloride is completely insoluble in toluene and xylene and can easily be removed from the reaction mixture by filtration.

After the solution from which ammonium chloride has been removed has been concentrated the isobutyramide crystallizes out in a purity such that it can be directly incorporated in drugs without further purification.

The product obtained by the process according to the invention is particularly suitable for producing pharmaceutical forms which contain isobutyramide either as the sole active substance or together with other active substances. Examples of such forms are sachets, syrups and inspissated syrups.

The following example describes the process according to the invention and a possible use for the product.

EXAMPLE

A solution of 35 kg of isobutyryl chloride in 250 l of toluene is cooled to −15°. 17 kg of ammonia (liquid) are metered in over the course of 2 h. The temperature rises to 30° C. during this. The mixture is then stirred for one hour while cooling to 18° C., and is then heated to reflux, the ammonium chloride which is formed is removed by filtration, the filter residue is washed four times with 25 l of toluene, and the filtrate is concentrated by removing 150 l of toluene by distillation. On cooling, 24.8 kg of isobutyramide (88.2% yield) crystallize out in a purity of 99.87%.

In order to produce a drug form from this, 4,000 g of isobutyramide, 5,950 g of sucrose and 50 g of flavoring are mixed together, and 10 g portions of the mixture are packed into sachets. The sachets are added to water before use.

We claim:

1. A process for preparing high-purity isobutyramide from isobutyryl chloride and ammonia, which comprises adding ammonia to a solution of isobutyryl chloride in toluene or xylene at −15° to 30° C., subsequently heating the mixture, removing the ammonium chloride which is formed by hot filtration, and allowing isobutyramide to crystallize out of the organic solution.

2. The process of claim 1, wherein the molar ratio of ammonia to isobutyryl chloride is from 2:1 to 4:1.

* * * * *